United States Patent [19]  [11] 4,138,587
Yamasaki et al.  [45] Feb. 6, 1979

[54] PROCESS FOR THE PREPARATION OF DIALKYL OXALATES

[75] Inventors: Toshiharu Yamasaki; Masao Eguchi; Schinichiro Uchiumi; Keigo Nishihira; Masayoshi Yamashita, all of Ube; Hiroshi Itatani, Ichihara, all of Japan

[73] Assignee: Ube Industries, Ltd., Ube, Japan

[21] Appl. No.: 817,996

[22] Filed: Jul. 22, 1977

[30] Foreign Application Priority Data
Jul. 27, 1976 [JP] Japan .................. 51/88673

[51] Int. Cl.$^2$ ............... C07C 67/36; C07C 69/36
[52] U.S. Cl. ................................. 560/204
[58] Field of Search ........................ 560/204

[56] References Cited

U.S. PATENT DOCUMENTS

| | | | |
|---|---|---|---|
| 3,393,136 | 7/1968 | Fenton et al. | 560/204 |
| 3,994,960 | 11/1976 | Yamazaki et al. | 560/204 |

FOREIGN PATENT DOCUMENTS

| | | | |
|---|---|---|---|
| 2213435 | 10/1973 | Fed. Rep. of Germany | 560/204 |
| 51-157311 | 12/1975 | Japan | 560/204 |
| 51-92428 | 3/1976 | Japan | 560/204 |

Primary Examiner—Jane S. Myers
Attorney, Agent, or Firm—Flynn & Frishauf

[57] ABSTRACT

A process for the preparation of dialkyl oxalates by reacting an aliphatic alcohol with carbon monoxide under pressure, which comprises carrying out the reaction in the presence of
(a) a catalyst comprising a platinum group metal or a salt thereof, and
(b) an accelerator composed of one or more compounds selected from the group consisting of nitric acid and nitrogen oxides.

12 Claims, No Drawings

PROCESS FOR THE PREPARATION OF DIALKYL OXALATES

This invention relates to a process for preparing dialkyl oxalates. More particularly, this invention relates to an improvement in a process for preparing a dialkyl oxalate by the reaction of an aliphatic alcohol with carbon monoxide.

Dialkyl oxalates have various industial utilities, for instance, as reagents for analysis, solvents, and starting materials for oxamide, orotic acid, etc.

In general, dialkyl oxalates have been heretofore prepared by reacting an aliphatic alcohol with carbon monoxide in the presence of a catalyst. As the catalyst of the reaction, a salt of a platinum group metal have reportedly been used necessarily in combination with a salt of iron or copper.

U.S. Pat. No. 3,393,136 of Donald M. Fenton et al. discloses a process for preparing dialkyl oxalates (hereinafter referred to as "prior process") wherein an aliphatic alcohol is contacted with carbon monoxide and oxygen under pressure in the presence of a catalyst composed of a mixture of a salt of a platinum group metal and a salt of copper or iron. However, said prior process is performed under anhydrous conditions, preferably, by employing an alkyl orthoformic ester as a dehydrating agent, since the production of a dialkyl oxalate is prevented by water formed in situ according to the reactions taking place.

The principal reaction is supposed to proceed as follows:

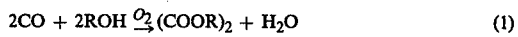

The side reactions are supposed as follows:

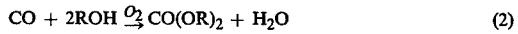

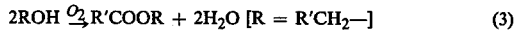

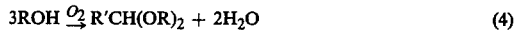

We have followed up this fact by our experiments and confirmed that a dialkyl oxalate is in no way formed unless any dehydrating agent is employed. Moreover, according to our experiments, it is required in the prior process that the reaction should be conducted under completely anhydrous conditions by the use of a dehydrating agent, since a yield of a dialkyl oxalate is extremely lowered due to the presence of even a minor amount of water in the reaction system, and thus very difficult and complicated procedures and control are required. Moreover, a dehydrating agent, particularly an alkyl orthoformic ester, is not only highly expensive but also convertible to an entirely different compound during the dehydration reaction so that this converted compound is incapable of being practically reused as a dehydrating agent. Therefore, a production cost of dialkyl oxalates becomes highly expensive in the prior process. Further, in the prior process, the selectivity of a dialkyl oxalate seems to be very low due to the by-production of a large amount of dialkyl carbonates, aliphatic carboxylates and the like, which is believed to be caused by the presence of a large amount of a dehydrating agent. Accordingly, the prior process seems to be commercially unsatisfactory.

We have conducted research in order to improve the prior process and to find out a commercially advantageous process for preparing dialkyl oxalates. More specifically, the experiments have been made for the purpose of finding out a reaction accelerator having the following characteristic: A dialkyl oxalate can be economically produced, even in the presence of water in the reaction system, by the addition of a minor amount of the reaction accelerator into the system instead of a large amount of a dehydrating agent.

As a result of our studies, it has been found that a dialkyl oxalate can be produced in a high yield and a high selectivity, even in the presence of water, by reacting an aliphatic alcohol with carbon monoxide under pressure in the presence of (a) a catalyst comprising a platinum group metal or a salt thereof and (b) an accelerator composed of one or more compounds selected from the group consisting of nitric acid and nitrogen oxides; molecular oxygen need not necessarily be introduced from outside since an accelerator such as nitric acid and nitrogen oxides acts as an oxidant to generate oxygen but dialkyl oxalates can be produced in higher yield and selectivity by introducing molecular oxygen into the reaction system; and this invention has been completed upon this finding.

According to the present invention, there is no need of the expensive dehydrating agent for keeping the reaction system under anhydrous conditions, of a salt of copper or iron which has been considered to be a necessary component for catalyst and of complicated procedures as required in the prior process, by the addition of a minor amount of a reaction accelerator into the reaction system, and also a dialkyl oxalate can be produced at an extremely lower production cost in comparison with the prior process. Moreover, a less amount of by-products such as dialkyl carbonates aliphatic carboxylates and the like is formed as compared with the prior process, and better yield and and selectivity of a dialkyl oxalate can be attained.

As the aliphatic alcohol which may be used as a starting material in the present process, an alcohol having 1 to 6 carbon atoms such as methanol, ethanol, n-propanol, isopropanol, n-butanol, isobutanol, n-amyl alcohol, isoamyl alcohol, n-hexanol and isohexanol may suitably be used for the purpose.

As the nitrogen oxide which may be used as an accelerator in the present invention, there may be mentioned nitrogen monoxide, nitrogen dioxide, dinitrogen trioxide, dinitrogen tetroxide, dinitrogen pentoxide, etc., preferably nitrogen dioxide.

The amount of such reaction accelerator, including nitric acid, to be added may somewhat vary upon the kind of the reaction accelerator, but it is desirable in view of the yield and selectivity of a dialkyl oxalate to employ the accelerator at 100–50,000 moles, preferably 500–10,000 moles, based on one mole of the catalyst.

As the catalyst which may be used in the present process, there may be mentioned a platinum group metal such as platinum, palladium, rhodium, iridium, preferably palladium and the salt thereof such as nitrate, chloride, sufate, phosphate, preferably a salt of palladium.

The amount of the catalyst mentioned above is of 0.0001–2.0 g., preferably 0.001–0.5 g., per 100 ml. of the aliphatic alcohol which is to be used as a starting material.

In cases where the present invention is applied industrially, these catalysts may be used by depositing on a carrier such as active carbon, silica gel, alumina, silica alumina, diatomaceous earth, magnesia, pumice, molecular sieve in order to recover readily these catalysts or a product formed.

The reaction of the present invention may be carried out in the absence of a solvent, but it is usually advantageous to conduct the reaction in the presence of an appropriate amount of a solvent such as benzene, nitrobenzene, chlorobenzene, cyclohexane, n-hexane, methylethyl ketone, toluene, esters of aliphatic carboxylic acids, diesters of aliphatic dicarboxylic acids, carbonic diesters, esters of aromatic carboxylic acids, acetophenone and so on, because not only the solvent may prevent the production of by-products to enhance the selectivity of the desired dialkyl oxalate but also the catalyst is dissolved in the organic solvent when the product is separated by distillation after reaction and can readily be circulated and reused so that the loss of the catalyst can be lowered.

In this invention, it is desirable to press carbon monoxide into a reaction vessel so that the carbon monoxide pressure is 40–120 Kg./cm$^2$G (G means gauge pressure), since the reaction rate is slower and the yield and selectivity of a dialkyl oxalate are lowered at a pressure less than 40 Kg./cm$^2$G, while the yield and the selectivity of a dialkyl oxalate remain approximately constant even at a pressure more than 120 Kg./cm$^2$G. In cases where molecular oxygen such as oxygen gas, air and other oxygen-containing gas obtained by diluting oxygen with an inert gas, e.g., nitrogen gas, the oxygen pressure usually is not more than 10 Kg./cm$^2$ so that a composition of the gas within a reaction vessel may be out of an explosive range and it is preferable for ensuring safety to press 2 or 3 divided portions of O$_2$ into the vessel.

The reaction temperature and period are preferably such that the reaction is effected for 0.5–5 hours at 60°–150° C., more preferably 80°–120° C. After completion of the reaction, a dialkyl oxalate may be obtained by conventional procedures such as cooling, recovery of the catalyst and reaction accelerator or distillation.

This invention is more concretely explained by way of the following examples and comparative example.

In each example, the product after completion of the reaction was quantitatively analyzed by gas chromatography and the results are summarized in Tables 1 and 2.

EXAMPLE 1

100 ml. of methanol was charged into an autoclave. Then, 0.04 g of metallic palladium and 1.82 g. of 70%-nitric acid were added thereto and carbon monoxide was pressed into the autoclave so as to be 80 Kg./cm$^2$ G. The content of the autoclave was heated to 110° C. and 8 Kg./cm$^2$ of oxygen was pressed thereinto in two divided portions. The reaction was carried out at 110° C. with stirring for one hour.

EXAMPLES 2–6

Each experiment was run in the same manner as in Example 1 except that 100 ml. of ethanol (Example 2.), n-propanol (Example 3.), n-butanol (Example 4.), n-amyl alcohol (Example 5.) or n-hexanol (Example 6.) was used as an aliphatic alcohol. The results of Examples 1–6 are shown in Table 1.

Table 1.

| Example No. | Aliphatic alcohol | Yield(mmol.) Dialkyl oxalate | Dialkyl carbonate | Aliphatic carboxylate |
|---|---|---|---|---|
| 1 | methanol | dimethyl oxalate 49.1 | dimethyl carbonate 1.7 | methyl formate 0 |
| 2 | ethanol | diethyl oxalate 45.9 | diethyl carbonate 1.2 | ethyl acetate trace |
| 3 | n-propanol | di-n-propyl oxalate 39.2 | di-n-propyl carbonate 1.3 | n-propyl propionate 0 |
| 4 | n-butanol | di-n-butyl oxalate 32.7 | di-n-butyl carbonate 2.4 | n-butyl butyrate 0 |
| 5 | n-amyl alcohol | di-n-amyl oxalate 29.5 | di-n-amyl carbonate 1.5 | n-amyl valerate trace |
| 6 | n-hexanol | di-n-hexyl oxalate 26.2 | di-n-hexyl carbonate 3.3 | n-hexyl caproate trace |

EXAMPLE 7

Into an autoclave were introduced 50 ml. of n-butanol and 50 ml. of di-n-butyl adipate. After addition of 0.2 g. of active carbon carrying 0.004 g. of metallic palladium and 0.91 g. of 70%-nitric acid, carbon monoxide was pressed thereinto so as to be 100 Kg./cm$^2$ G. Then, the content of the autoclave was heated to 100° C. After pressing 8 Kg./cm$^2$ of oxygen thereinto in two divided portions, the reaction was carried out with stirring at 100° C. for one hour.

EXAMPLE 8

An experiment was run in the same manner as in Example 7 except that dibutyl adipate was not used.

EXAMPLES 9–12

Each experiment was run in the same manner as in Example 7 except that 2 g. of active carbon carrying 0.04 g. of metallic platinum (Example 9.), 0.023 g. of palladium nitrate (Exampel 10.), 0.027 g. of platinum chloride (Example 11.) or 0.02 g. of palladium sulfate (Example 12.) was used as a catalyst.

EXAMPLE 13

An experiment was run in the same manner as in Example 7 except that 0.50 g. of liquid nitrogen dioxide was used in place of nitric acid.

EXAMPLE 14

An experiment was run in the same manner as in Example 1 except that 1.80 g. of 70%-nitric acid was used and oxygen was not introduced into the reaction system.

COMPARATIVE EXAMPLE 1

An experiment was run in the same manner as in Example 7 except that nitric acid was not used.

The results of Examples 9–14 and Comparative example 1. are shown in Table 2.

Table 2.

| Example No. | Catalyst | Yield (mmol.) di-n-butyl oxalate | di-n-butyl carbonate | n-butyl butyrate |
|---|---|---|---|---|
| 7 | Pd-C | 40.2 | 0.3 | 0 |
| 8 | " | 41.9 | 2.7 | 0.5 |
| 9 | Pt-C | 19.1 | 1.2 | 1.1 |
| 10 | Pd(NO$_3$)$_2$ | 54.2 | 0.3 | 0.2 |
| 11 | PtCl$_2$ | 26.4 | 2.3 | 0.7 |

Table 2.-continued

| Example No. | Catalyst | Yield (mmol.) | | |
|---|---|---|---|---|
| | | di-n-butyl oxalate | di-n-butyl carbonate | n-butyl butyrate |
| 12 | PdSO$_4$ | 35.5 | 0.6 | 0.2 |
| 13 | Pd-C | 51.6 | 0.5 | 0.2 |
| 14 | " | 8.0 | 0 | 0 |
| Comp.Exp. 1 | Pd-C (without HNO$_3$) | 4.0 | 0 | 0 |

What is claimed is:

1. A process for the preparation of dialkyl oxalates by reacting an alkanol having from 1 to 6 carbon atoms with carbon monoxide under pressure, which comprises carrying out the reaction in the presence of
   (a) a catalytic amount of a catalyst comprising a platinum group metal or a salt thereof,
   (b) an accelerating amount of an accelerator composed of one or more compounds selected from the group consisting of nitric acid and nitrogen oxides, and
   (c) molecular oxygen.

2. The process as claimed in claim 1, in which said accelerator is selected from the group consisting of nitric acid and nitrogen dioxide.

3. The process as claimed in claim 1, in which the platinum group metal is palladium.

4. The process as claimed in claim 1, in which the salt of the platinum group metal is a salt of palladium.

5. The process as claimed in claim 1, in which the catalyst is used in an amount of 0.0001–2.0 g. per 100 ml. of the aliphatic alcohol.

6. The process as claimed in claim 1, in which the catalyst is used in an amount of 0.001–0.5 g. per 100 ml. of the aliphatic alcohol.

7. The process as claimed in claim 1, in which the accelerator is employed in a molar amount of 100–50,000 times the catalyst.

8. The process as claimed in claim 1, in which the accelerator is employed in a molar amount of 500–10,000 times the catalyst.

9. The process as claimed in claim 6, in which the accelerator is employed in a molar amount of 500–10,000 times the catalyst.

10. The process as claimed in claim 1, in which the reaction temperature is between 60° and 150° C.

11. The process as claimed in claim 1, in which the reaction temperature is between 80° and 120° C.

12. The process as claimed in claim 1, in which carbon monoxide pressure is between 40 and 120 Kg./cm$^2$G.

* * * * *